(12) United States Patent
Kohno

(10) Patent No.: US 8,182,419 B2
(45) Date of Patent: May 22, 2012

(54) ENDOSCOPE WITH SUCTIONING MEANS

(75) Inventor: Shinichi Kohno, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1043 days.

(21) Appl. No.: 11/392,709

(22) Filed: Mar. 30, 2006

(65) Prior Publication Data
US 2006/0229498 A1 Oct. 12, 2006

(30) Foreign Application Priority Data

Mar. 31, 2005 (JP) ............................... P.2005-103070

(51) Int. Cl.
*A61B 1/12* (2006.01)
(52) U.S. Cl. ...................................... 600/158; 600/159
(58) Field of Classification Search .................. 600/133, 600/156–159; 417/145, 147–149, 152–154
See application file for complete search history.

(56) References Cited

U.S. PATENT DOCUMENTS

| 3,499,393 A * | 3/1970 | Bent ............................... 604/149 |
|---|---|---|
| 5,832,920 A * | 11/1998 | Field ......................... 128/207.14 |
| 2001/0039370 A1* | 11/2001 | Takahashi et al. ............. 600/159 |
| 2004/0049217 A1* | 3/2004 | Ross et al. ..................... 606/171 |
| 2005/0005936 A1* | 1/2005 | Wondka ..................... 128/204.18 |

FOREIGN PATENT DOCUMENTS

| JP | 2003-52620 A | 2/2003 |
| JP | 2003-70737 A | 3/2003 |

* cited by examiner

*Primary Examiner* — Matthew J Kasztejna
*Assistant Examiner* — Ryan Henderson
(74) *Attorney, Agent, or Firm* — Birch, Stewart, Kolasch & Birch, LLP

(57) ABSTRACT

An endoscope comprises: an insertion portion to be inserted into a body cavity; an operation portion continuously provided from a proximal end side of the insertion portion; and a suction section that performs suction from an distal end of the insertion portion, wherein the suction section comprises: a cylinder in which a gas is compressed and filled; a nozzle unit that generates a negative pressure inside the nozzle unit by jetting out the gas in the cylinder; and a liquid receiver tank communicated with the distal end of the insertion portion, the negative pressure inside the nozzle unit being transmitted to the liquid receiver tank.

4 Claims, 14 Drawing Sheets

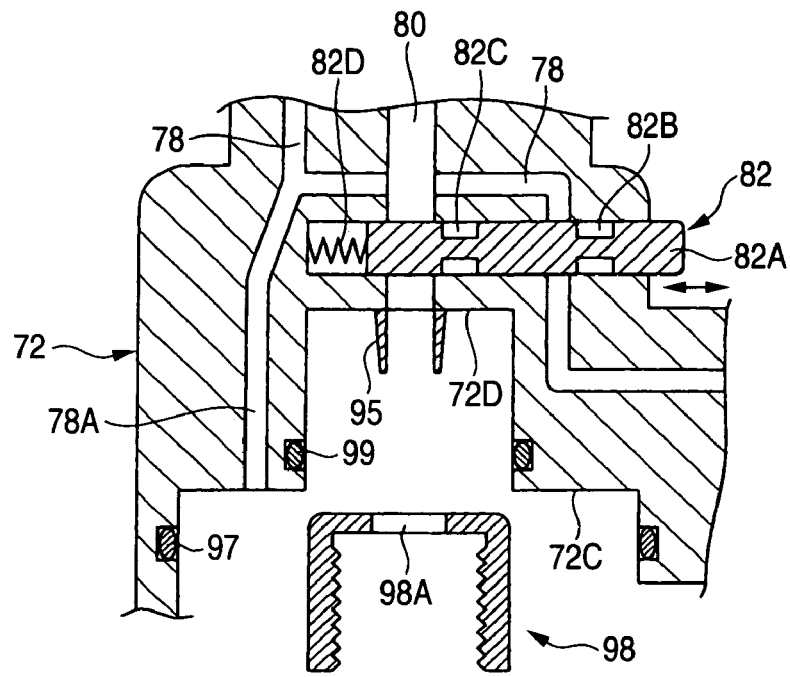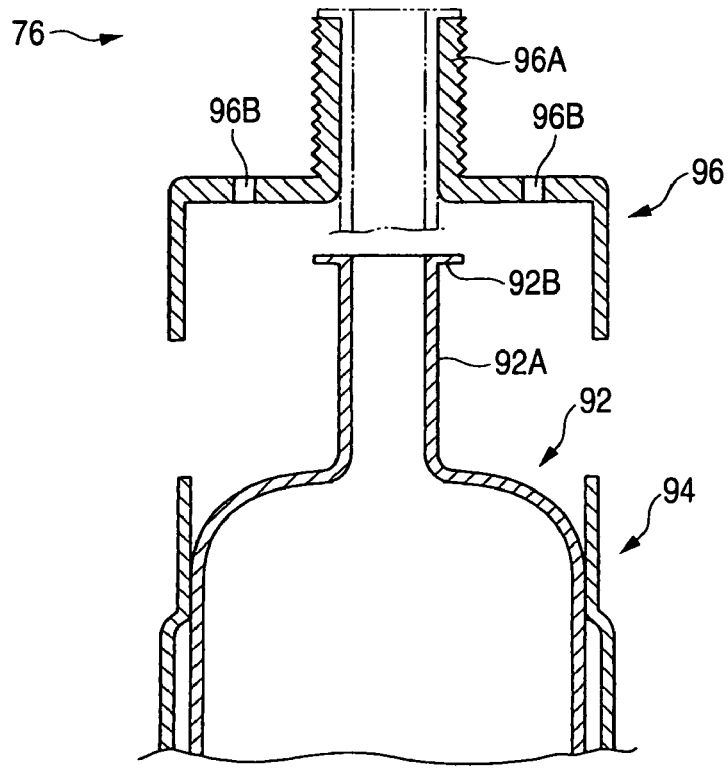
FIG. 7

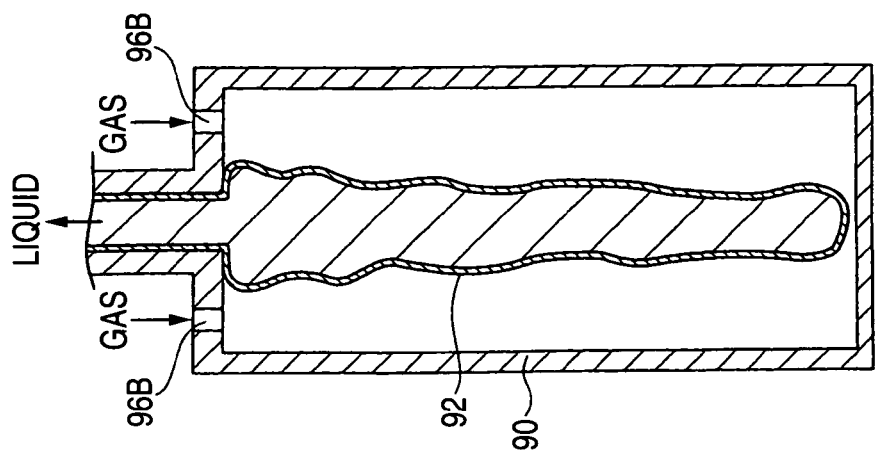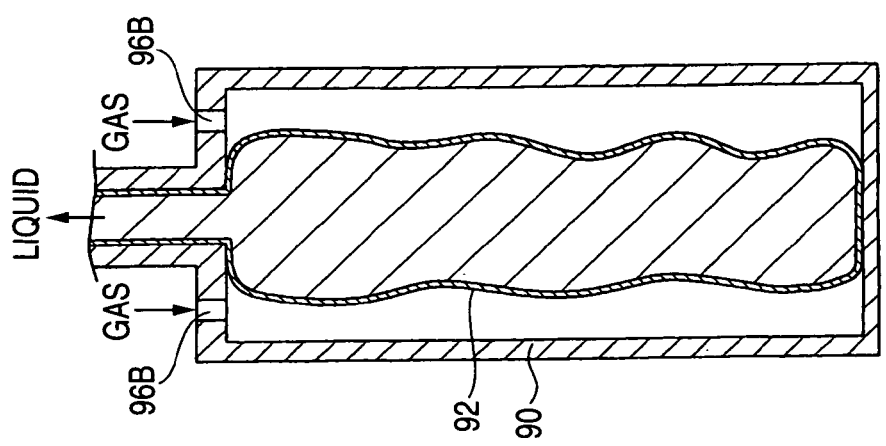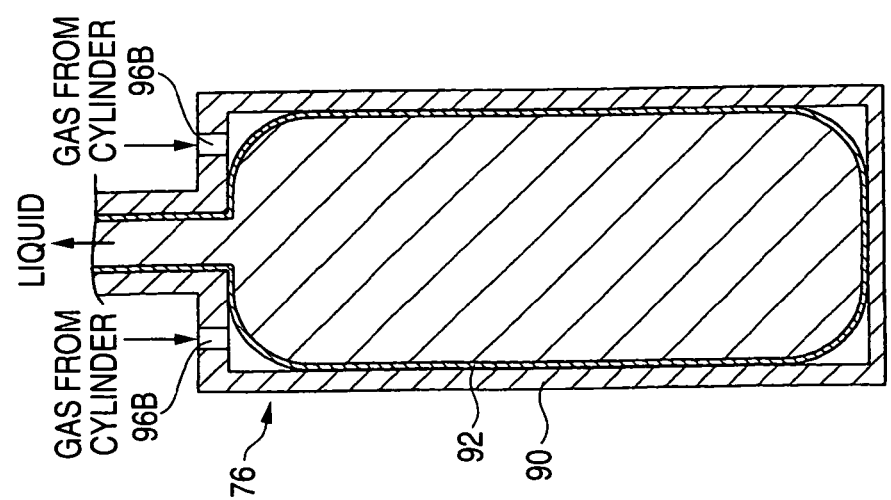

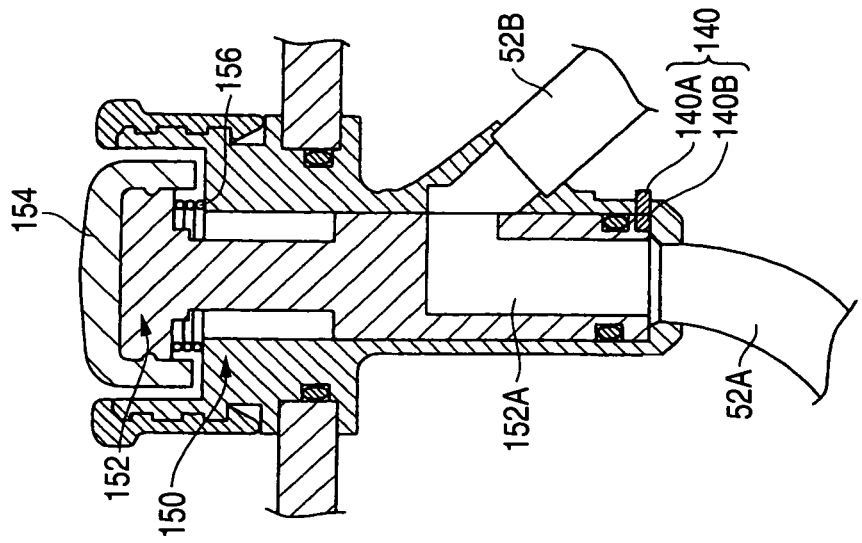
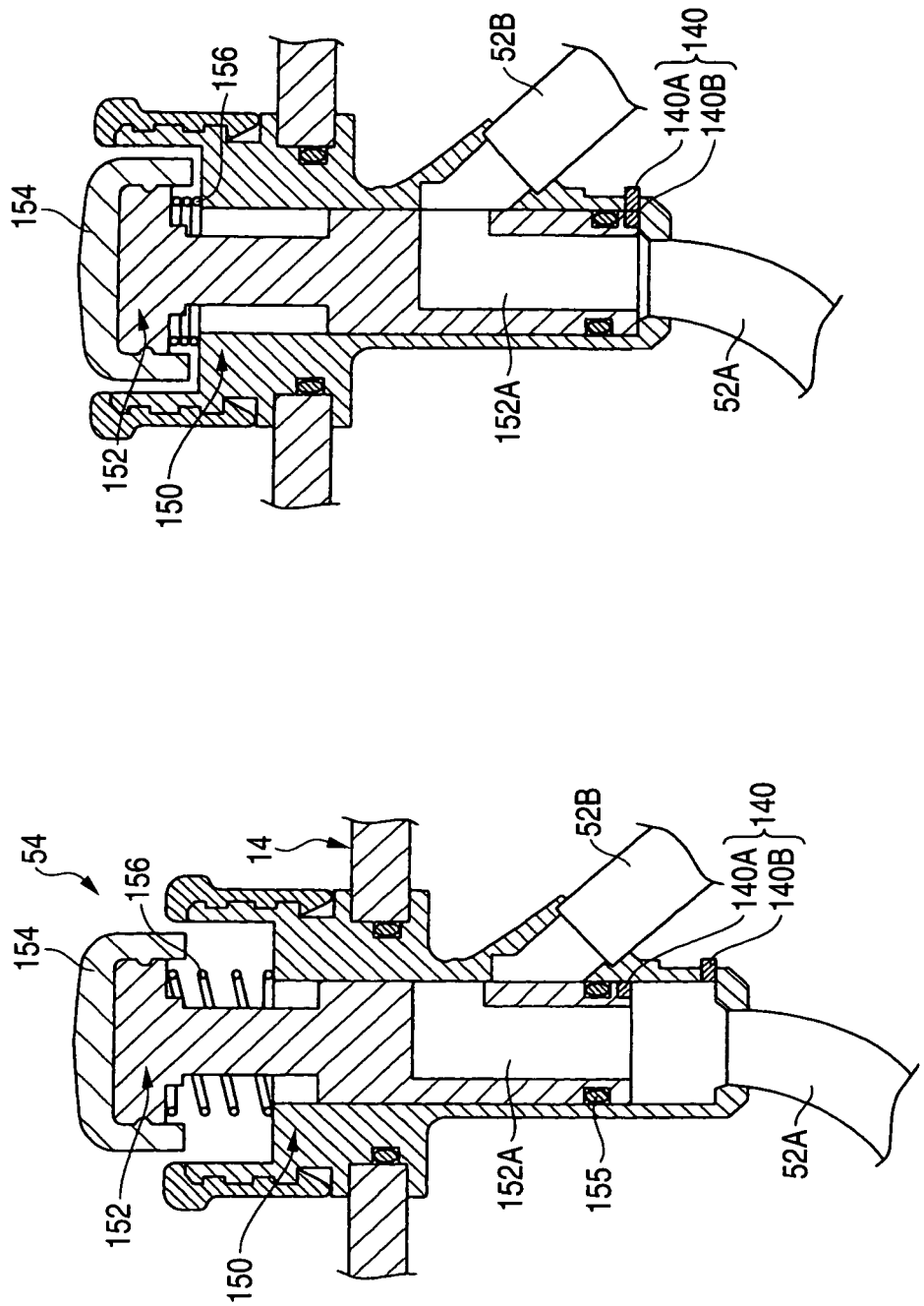

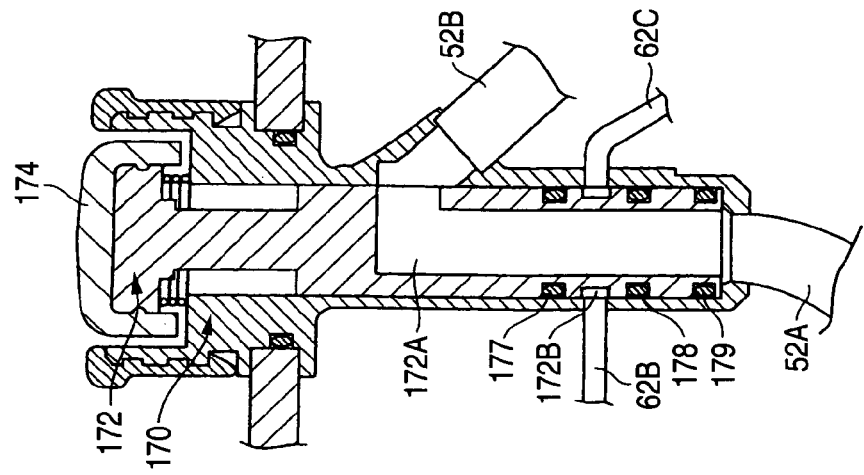
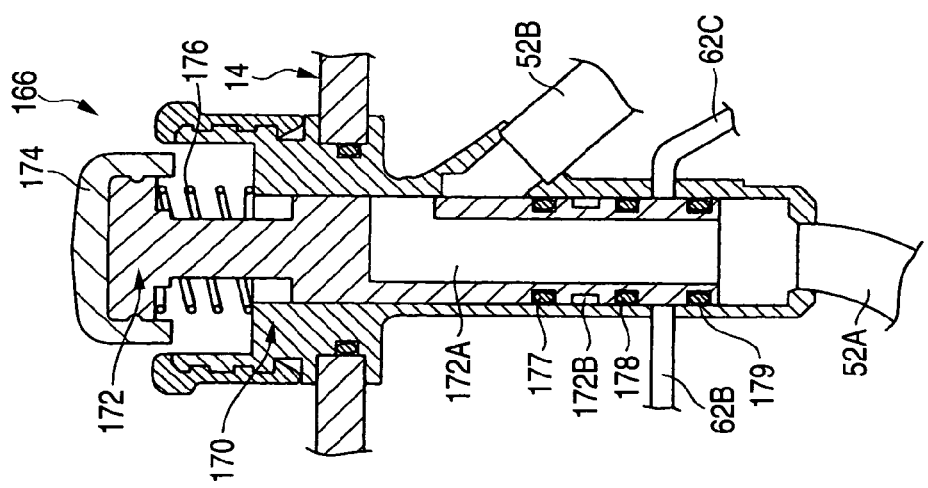

ENDOSCOPE WITH SUCTIONING MEANS

BACKGROUND OF THE INVENTION

1. Field of the Invention

The present invention relates to an endoscope, and in particular, to an endoscope having a suction section that performs suction from a distal end of an insertion portion.

2. Description of the Related Art

An endoscope has an operation portion to be held by an operator and performs observation of the inside of a body cavity by inserting an insertion portion continuously provided from the operation portion. The operation portion is conventionally provided with a universal cable extending from it, and a connector and the like provided at the distal end of the universal cable are connected to a peripheral apparatus such as a light source device or a processor and used. Therefore, the use range of the conventional endoscope is limited by the length of the universal cable, so that free movement while using the endoscope is impossible. In addition, during operation of the operation portion, the universal cable becomes entangled and obstructs the operation, resulting in low operability.

To solve this problem, a portable endoscope having no cable to connect the peripheral apparatus and the endoscope has been proposed. For example, in JP-A-2003-52620 and JP-A-2003-70737, endoscopes including an air/water-feeding pump, a water tank, and a pump-driving battery attached to the operation portion are described.

However, JP-A-2003-52620 and JP-A-2003-70737 include no detailed description about a suction means for suctioning from the distal end of the insertion portion. To secure a sufficient suction force in an endoscope, generally, a large suction pump is needed, and if such a suction pump is installed in the operation portion, the operation portion is increased in size and weight, resulting in poor portability.

In addition, if the suction pump is provided, a large battery for driving the suction pump becomes necessary, and if this battery is installed in the operation portion, the operation portion is further increased in size and weight.

Therefore, conventional endoscopes use suction equipment installed in hospitals as suction means, and perform suctioning by connecting a suction connector set in each room of the hospital and a suction connector of the endoscope via a tube. Therefore, conventional endoscopes are not usable at a site without a suction connector of a hospital, or cannot be carried about ready for use, so that its portability is poor.

SUMMARY OF THE INVENTION

The invention was made in view of these circumstances, and an object thereof is to provide an endoscope that has a suction section that performs suction from the distal end of the insertion portion and is excellent in portability.

In order to achieve the object, according to a first aspect of the invention, an endoscope comprises: an insertion portion to be inserted into a body cavity; an operation portion continuously provided from a proximal end side of the insertion portion; and a suction section that performs suction from an distal end of the insertion portion, wherein the suction section comprises: a cylinder in which a gas is compressed and filled; a nozzle unit that generates a negative pressure inside the nozzle unit by jetting out the gas in the cylinder; and a liquid receiver tank communicated with the distal end of the insertion portion, the negative pressure inside the nozzle unit being transmitted to the liquid receiver tank.

According to the first aspect of the invention, since a suction force is generated by the nozzle unit by using the gas in the cylinder, the electric power for suctioning becomes unnecessary, whereby the power consumption of the endoscope can be reduced. Therefore, a small-sized light-weight battery can be used as a power source of the endoscope, and by installing this battery in the operation portion, the operation portion can be reduced in weight and size.

According to the first aspect of the invention, since a suction force is generated by the cylinder and the nozzle unit, the endoscope can be used at a site without suction equipment.

According to a second aspect of the invention, in the first aspect of the invention, the cylinder, the nozzle unit, and the liquid receiver tank are integrally formed as a suction unit separated from the operation portion.

According to the second aspect of the invention, the cylinder, the nozzle unit, and the liquid receiver tank are integrally formed as a suction unit, so that the duct construction of the endoscope can be simplified.

According to a third aspect of the invention, in the first aspect of the invention, an air-feed section to feed the gas in the cylinder to the distal end of the insertion portion is provided.

According to the third aspect of the invention, one cylinder is commonly used as the cylinder of the air-feed section for feeding air to the distal end of the insertion portion and the cylinder of the suction section, so that the system can be reduced in size and weight.

According to a fourth aspect of the invention, in the third aspect of the invention, the cylinder is attached to the operation portion. According to the fourth aspect of the invention, the cylinder of the air-feed section is attached to the operation portion, so that the cable to connect the air-feed section and the operation portion becomes unnecessary, whereby increasing the portability.

BRIEF DESCRIPTION OF THE DRAWINGS

FIG. 7 is an exploded view of the water-feeding unit;

FIGS. 9A to 9C are explanatory views of working of the water-feeding unit;

FIGS. 12A and 12B are sectional views of a construction of a suction valve;

FIGS. 15A and 15B are sectional views of a construction of the suction valve of FIG. 14.

DETAILED DESCRIPTION OF THE INVENTION

Figure 1:
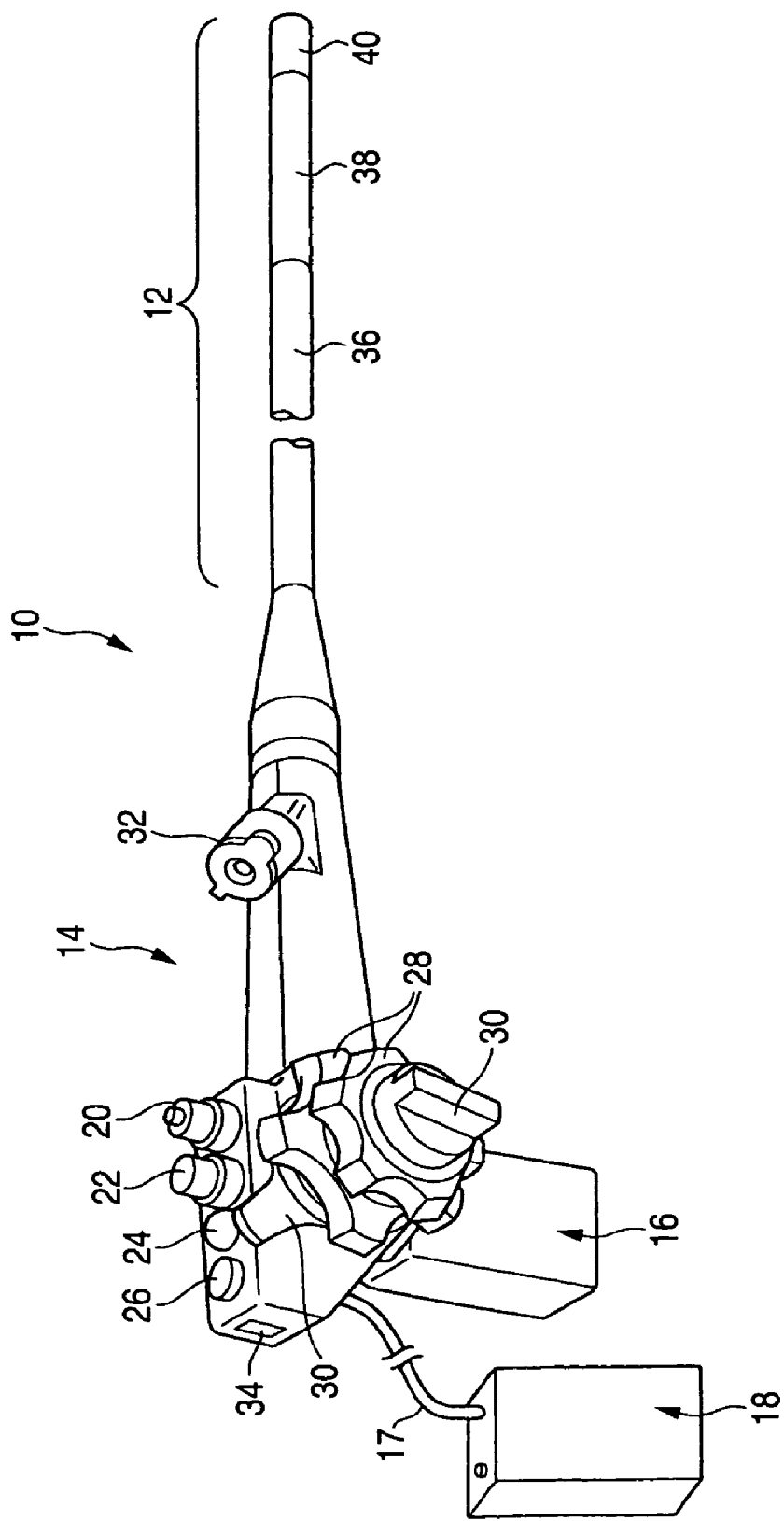
FIG. 1 is a construction view of an endoscope according to the invention.

Hereinafter, a preferred embodiment of an endoscope according to the invention is described in detail with reference to the accompanying drawings. FIG. 1 is a construction view of an embodiment of the endoscope of the invention.

As shown in FIG. 1, the endoscope 10 mainly comprises an insertion portion 12 to be inserted into a body cavity, an operation portion 14 continuously provided on the proximal end side of the insertion portion 12, an air/water-feeding unit 16 attached to the operation portion 14, and a separated suction unit 18 connected to the operation portion 14 via a tube 17.

At the operation portion 14, an air/water-feeding button 20, a suction button 22, a shutter button 24, and a function switching button 26 are arranged in parallel, and a pair of angle knobs 28 and 28 and lock levers 30 and 30 for locking the angle knobs 28 are provided. On the distal end side of the operation portion 14, a forceps insertion portion 32 is provided, and on the proximal end side of the operation portion 14, a cover 34 is attached so as to open and close, and inside the cover 34, a battery housing for housing a small-sized battery (not shown) is provided. As the battery, for example, a gum-type rechargeable battery or a fuel cell is used, and by this battery, electric power is supplied to a CCD and an LED, etc., described later.

The insertion portion 12 comprises, in order from the operation portion 14 side, a flexible portion 36, a bending portion 38, and a distal end 40, and the bending portion 38 is remotely operated to bend by rotating the angle knobs 28 and 28 on the operation portion 14. Thereby, the distal end 40 can be turned to a desired direction.

Figure 2:
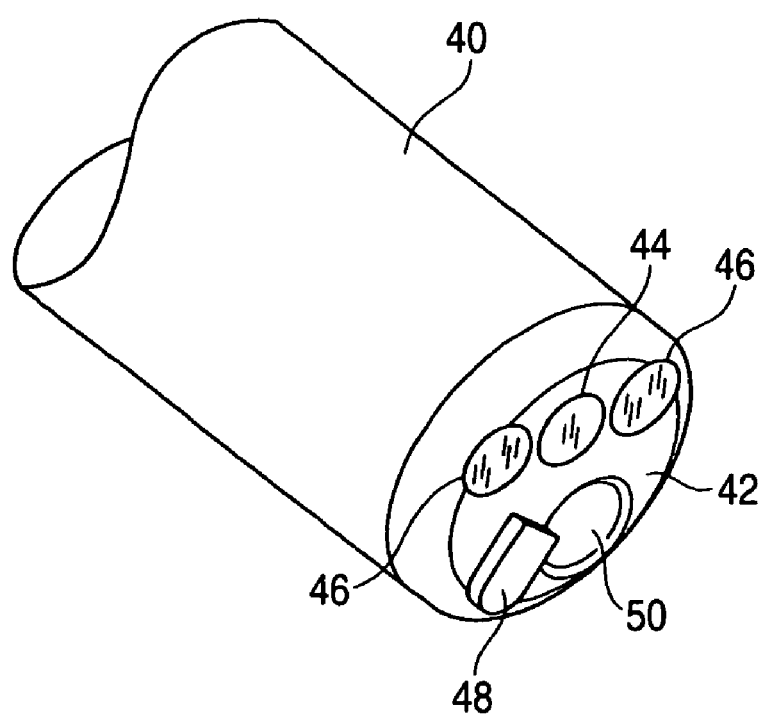
FIG. 2 is a perspective view showing the distal end of an insertion portion of the endoscope.

As shown in FIG. 2, on the distal end face 42 of the distal end 40, an observation optical system 44, illuminating optical systems 46 and 46, an air/water-feeding nozzle 48, and a forceps opening 50 are provided. A CCD (not shown) is disposed rearward of the observation optical system 44, and an observation image taken by the observation optical system 44 is formed on a photodetecting surface of the CCD and converted into electrical signals. The CCD is connected to an unillustrated communications section, and this communications section transmits the electrical signals to a processor (not shown), wirelessly. Then, the signals are converted into video signals by the processor, and the observation image is outputted to a monitor (not shown) connected to the processor.

An unillustrated LED is disposed rearward of the illuminating optical systems 46 and 46. This LED is wired to the battery housed inside the operation portion 14, and the LED is turned on by electrical power of the battery and illumination light is irradiated forward of the illuminating optical systems 46 and 46.

Figure 3:
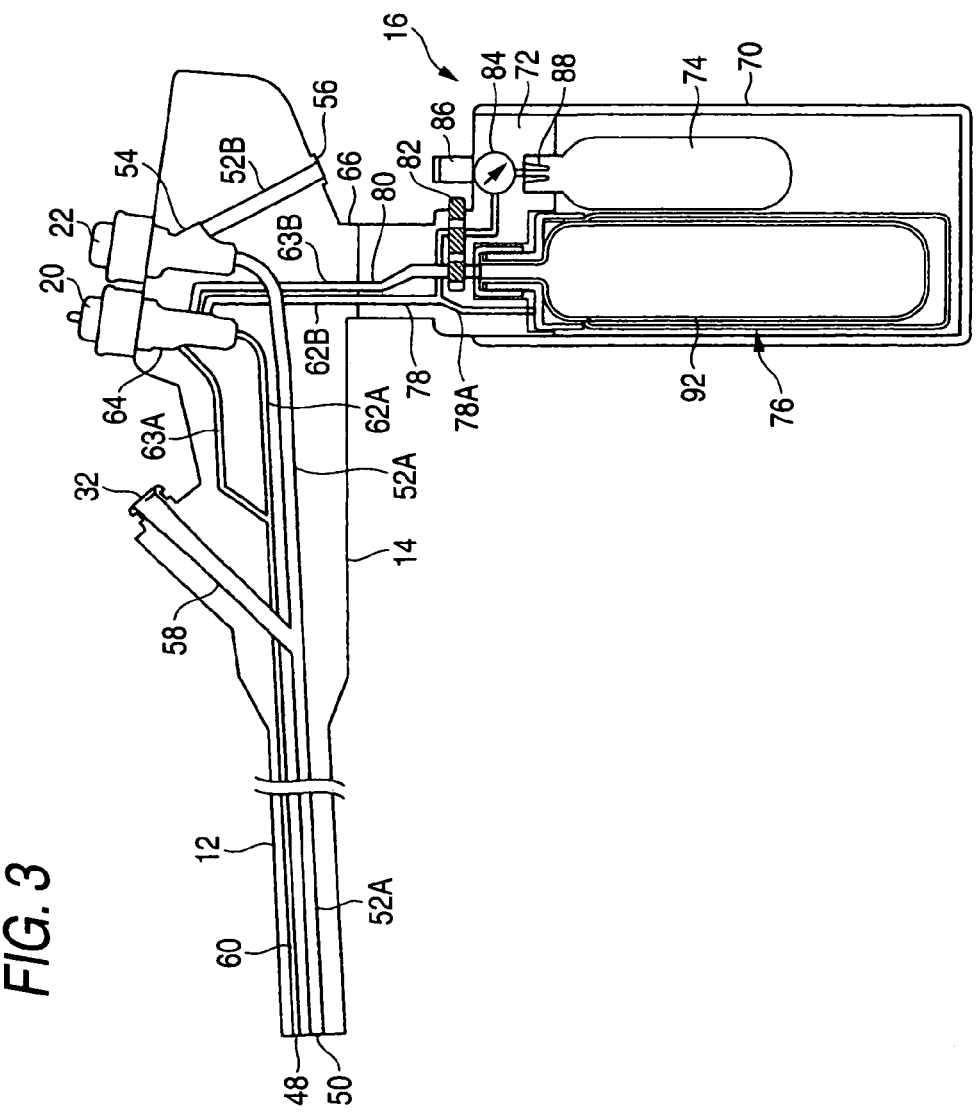
FIG. 3 is a duct construction view of the endoscope.

To the forceps opening 50, a suction tube 52A shown in FIG. 3 is connected. To this suction tube 52A, the distal end of a forceps tube 58 is connected, and the other end of the forceps tube 58 is disposed at a forceps insertion portion 32. Therefore, by inserting treatment equipment such as forceps from the forceps insertion portion 32, the treatment equipment can be led out from the forceps opening 50.

The suction tube 52A is connected to a suction valve 54 provided at the operation portion 14, and to this suction valve 54, a suction tube 52B is connected. The distal end of the suction tube 52B is disposed on a suction connector 56 provided at the operation portion 14. To the suction connector 56, a suction unit 18 (see FIG. 1) is connected via a suction tube 17 described later, and the suction tube 52B is imparted with a suction force. The suction valve 54 is controlled by the suction button 22, and this suction valve 54 switches communication and blockage between the suction tubes 52A and 52B. Therefore, by operating the suction button 22, the suction force of the suction tube 52B is transmitted to the suction tube 52A to suction a suctioning object such as the body fluid and filth from the forceps opening 50.

On the other hand, to the air/water-feeding nozzle 48, an air/water-feeding tube 60 is connected. The air/water-feeding tube 60 is branched into an air-feeding tube 62A and a water-feeding tube 63A, and these air-feeding tube 62A and water-feeding tube 63A are connected to an air/water-feeding valve 64. To the air/water-feeding valve 64, the air-feeding tube 62B and the water-feeding tube 63B are connected, and the ends of the air-feeding tube 62B and the water-feeding tube 63B are disposed at an air/water-feeding connector 66.

To the air/water-feeding connector 66, an air/water-feeding unit 16 is detachably attached. The construction of the air/water-feeding unit 16 is explained below.

Figure 4:
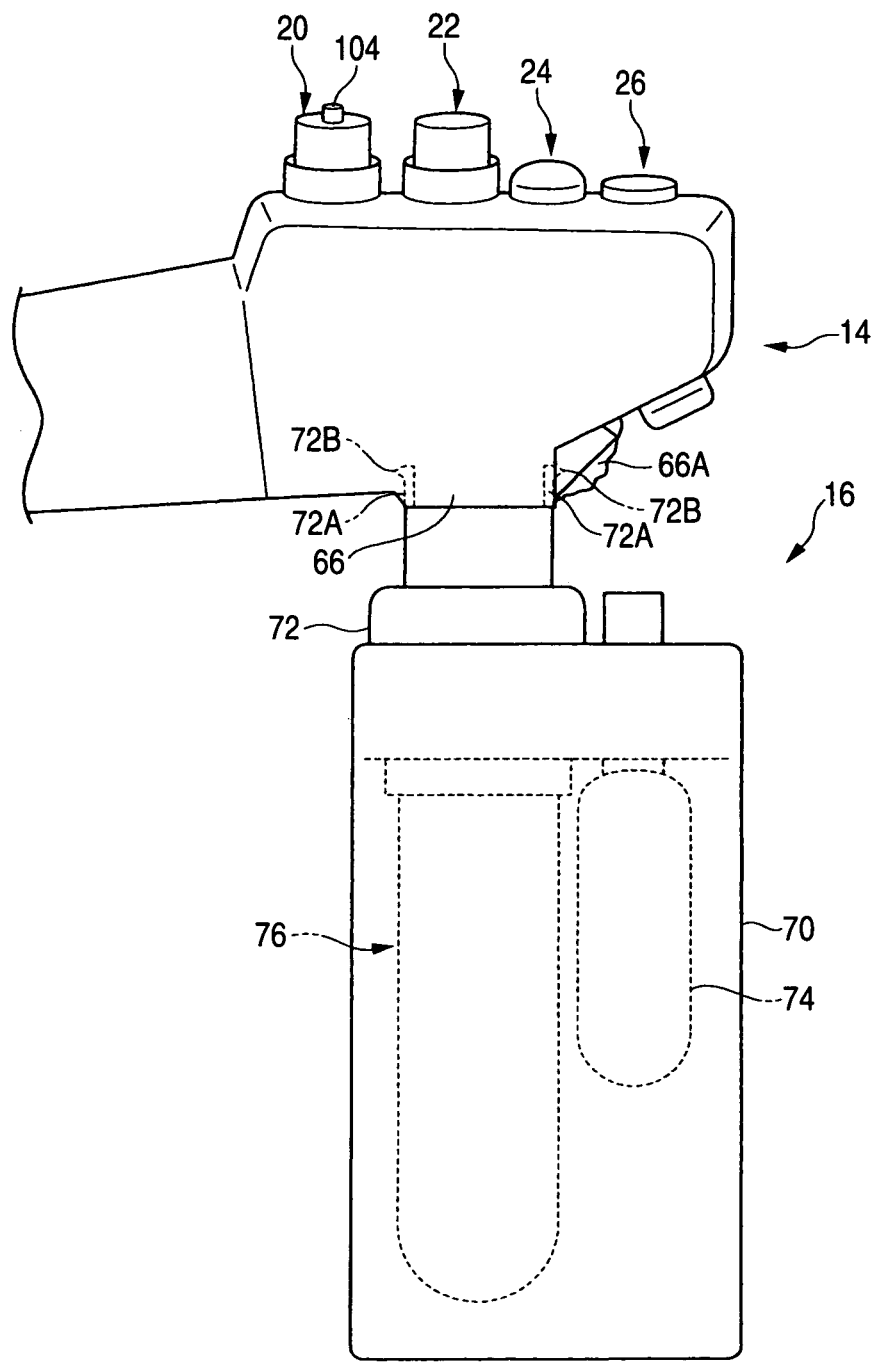
FIG. 4 is a side view of an air/water-feeding unit.
Figure 5:
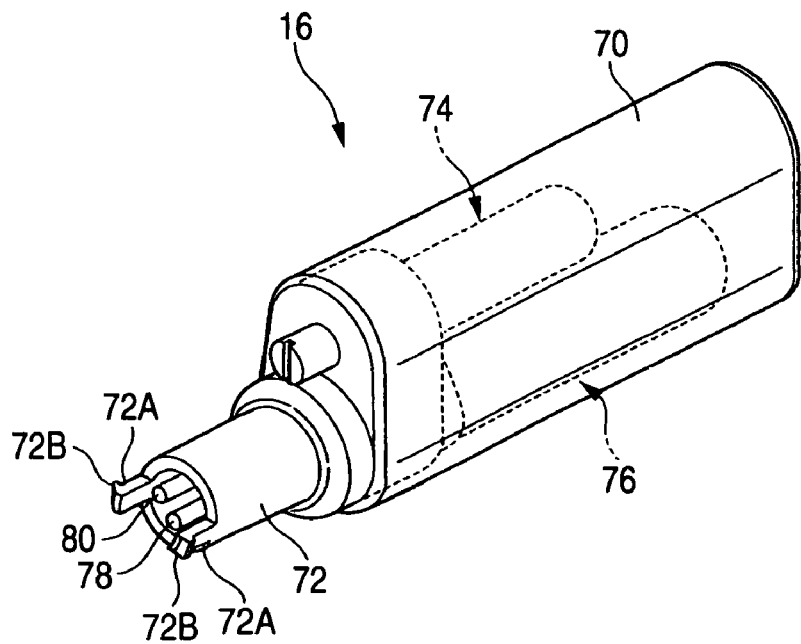
FIG. 5 is a perspective view of the air/water-feeding unit.

FIG. 4 is a side view of a state in that the air/water-feeding unit 16 is attached to the operation portion 14, and FIG. 5 is a perspective view of the air/water-feeding unit 16.

As shown in these figures, the air/water-feeding unit 16 is entirely formed into a thin and long rectangular shape. The air/water-feeding unit 16 is disposed so that its longitudinal direction becomes orthogonal to the longitudinal direction of the operation portion 14 when it is attached to the air/water-feeding connector 66. The air/water-feeding connector 66 is disposed on the proximal end side of the operation portion 14 on the side opposite to the suction button 22 and the air/water-feeding button 20. Therefore, by attaching the air/water-feeding unit 16 to the air/water-feeding connector 66, the air/water-feeding unit 16 is disposed between the forefinger and the thumb of an operator's hand holding the operation portion 14. Thereby, the air/water-feeding unit 16 does not become an obstacle when controlling the operation portion 14. As the attaching position and attaching direction of the air/water-feeding unit 16, a position that does not obstruct the operator's hand holding the operation portion 14 is selected although these are not especially limited. Therefore, for example, it is also possible that the air/water-feeding connector 66 is provided on the proximal end of the operation portion 14, and the air/water-feeding unit 16 is attached to the air/water-feeding connector 66 along the longitudinal direction of the operation portion 14.

The air/water-feeding unit 16 mainly comprises a hollow case 70, a coupling member 72 serving as a cover of this case 70, and a cylinder 74 and a water-feeding unit 76 housed inside the case 70. The cylinder 74 and the water-feeding unit 76 are detachably attached to the hard coupling member 72, and the end of this coupling member 72 is detachably attached to the air/water-feeding connector 66.

As a coupling mechanism between the coupling member 72 and the air/water-feeding connector 66, for example, a mechanism called snap fit is used. In this mechanism, as shown in FIG. 5, a projection 72A having a claw 72B outside is provided on the coupling side end of the coupling member 72, and a concave portion (not shown) to engage with the claw 72B of the projection 72A is formed on the air/water-feeding connector 66. Then, the claw 72B of the projection 72A of the coupling member 72 is engaged in the concave portion of the air/water-feeding connector 66, whereby the coupling member 72 and the air/water-feeding connector 66 are coupled to each other. Thereby, the coupling member 72 and the air/water-feeding connector 66 are coupled at a constant pulling-out strength. The air/water-feeding connector 66 of FIG. 4 is provided with a release lever 66A, and by operating this release lever 66A to slide, the claw 72B is pressed inward and the engagement with the concave portion is released. Thereby, the coupling between the air/water-feeding connector 66 and the coupling member 72 can be released.

The coupling mechanism between the coupling member 72 and the air/water-feeding connector 66 is not limited to the snap fit, and may be any coupling mechanism as long as it has a constant pulling-out strength. Therefore, for example, a tube fitting mechanism can also be used. In the tube fitting mechanism, a lock claw projecting from the inner circumferential surface of a cylindrical housing bites into a tube for secure coupling to the tube, and an open ring provided on the housing end is pressed in, whereby the open ring withdraws the lock claw outward and releases the engagement between the lock claw and the tube. It is also possible that such a tube fitting mechanism is used to couple the coupling member 72 to the air/water-feeding connector 66.

As shown in FIG. 3, an air-feeding duct 78 and a water-feeding duct 80 are provided inside the coupling member 72. The air-feeding duct 78 and the water-feeding duct 80 are communicated with the air-feeding tube 62B and the water-feeding tube 63B when the coupling member 72 is attached to the air/water-feeding connector 66. The distal end of the water-feeding duct 80 is communicated with a pouched member 92, described later, of the water-feeding unit 76, and the distal end of the air-feeding duct 78 is communicated with the cylinder 74. The air-feeding duct 78 is branched inside the coupling member 72, and the branched-feeding duct 78A is communicated with the inside of a housing case 90 of the water-feeding unit 76.

In the air-feeding duct 78 and the water-feeding duct 80, an opening and closing valve 82 is disposed, and this opening and closing valve 82 switches communication and blockage of the air-feeding duct 78 and the water-feeding duct 80. The construction of the opening and closing valve 82 is described later.

The air-feeding duct 78 is provided with a regulator 84 to keep constant the pressure of a gas flowing in the air-feeding duct 78. The regulator 84 is provided with an adjust screw 86, and by rotating this adjust screw 86, the pressure of the gas flowing in the air-feeding duct 78 can be adjusted. On the distal end of the air-feeding duct 78, a hollow pin 88 is projectedly provided, and at the position of this hollow pin 88, the cylinder 74 is screwed and attached.

In the cylinder 74, a gas to be fed (for example, an inactive gas such as $N_2$ or $CO_2$, or the air) is compressed and filled. Although the volume of the gas inside the cylinder 74 is not especially limited, and for example, a gas filled to approximately 4 liters is used, and replaced every time treatment for a patient is finished. The cylinder 74 is carried filled with the gas and sealed by a cover (not shown), and by screwing this cylinder 74 to the coupling member 72, the hollow pin 88 punctures the cover of the cylinder 74, whereby the inside of the cylinder 74 is communicated with the regulator 84. Thereby, a high-pressure gas inside the cylinder 74 is fed to the regulator 84, and this high-pressure gas is adjusted to a desired pressure by the regulator 84. Then, by opening the opening and closing valve 82, the gas is fed to the air-feeding tube 62B via the air-feeding duct 78, and fed to the water-feeding unit 76 via the branched-feeding duct 78A.

Figure 6:
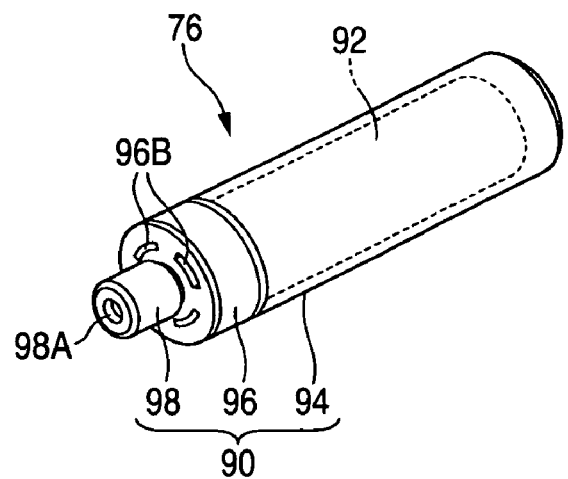
FIG. 6 is a perspective view of a water-feeding unit.

As shown in FIG. 6 and FIG. 7, the water-feeding unit 76 mainly comprises the hollow housing case 90 and the pouched member 92 housed inside the housing case 90. Inside the pouched member 92, a liquid to be fed (for example, water or sterile water) is filled. As a material of the pouched member 92, for example, aluminum film, plastic film or rubber is used, and the inner capacity thereof can be reduced. Namely, the pouched member 92 is crushed, deflated or shrunk so that its inner capacity becomes smaller. The pouched member 92 is projectedly provided with a cylindrical portion 92A, and a brim 92B is formed on the distal end outer circumference of the cylindrical portion 92A. The brim 92B is preferably made of an elastic material such as rubber. It is preferable that the pouched member 92 formed as described above is carried about while filled with a liquid and sealed by a cover on the distal end of the cylindrical portion 92A. The pouched member is preferably formed so that a hole opens at the distal end of the cylindrical portion 92A of the pouched member 92 when the water-feeding unit 76 is fitted to the coupling member 72.

On the other hand, the housing case 90 is formed by a bottomed cylindrical case main body 94, a cover member 96 serving as a cover of the case main body 94, and a cap member 98 to be attached to the distal end of the cover member 96. The case main body 94, the cover member 96, and the cap member 98 are made of, for example, plastic so as to have a sufficient strength, and to make it more difficult to deform than the pouched member 92. The housing case 90 is required so as to make it more difficult to deform than the pouched member 92, and for example, a case made of the same material as that of the pouched member 92 and formed thicker than the pouched member 92 can be used.

The case main body 94 and the cover member 96 of the housing case 90 are fitted. When fitting, the outer circumferential surface of the case main body 94 and the inner circumferential surface of the cover member 96 come into contact throughout the circumference, and the hermetically sealing at the contact surface is kept. When fitting, it is also possible that the case main body 94 and the cover member 96 are coupled by using the snap-fit mechanism or the tube fitting mechanism so that a predetermined pulling-out strength is secured.

As shown in FIG. 7, a cylindrical portion 96A is projectedly formed at the center of the end face of the cover member 96. The cylindrical portion 92A of the pouched member 92 is fitted in the cylindrical portion 96A of this cover member 96. A screw is formed on the outer circumferential surface of the cylindrical portion 96A of the cover member 96, and the cap member 98 is screwed and attached to this cylindrical portion 96A. The cap member 98 has a water passage hole 98A in its end face, and the cap member 98 is communicated with the inside of the pouched member 92 via this water passage hole 98A.

In the end face of the cover member 96, air passage holes 96B and 96B . . . are formed around the cylindrical portion 96A. The air passage holes 96B, 96B communicate the inside and the outside of the housing case 90 with each other, and are formed into, for example, arc shapes as shown in FIG. 6 at four points at intervals of 90 degrees.

The housing case 90 and the pouched member 92 are assembled as follows. Namely, first, the cylindrical portion 92A of the pouched member 92 is fitted in the cylindrical portion 96A of the cover member 96. At this time, the brim 92B of the cylindrical portion 92A of the pouched member 92 is inserted while being elastically deformed. After insertion, the brim 92B elastically restores to its original shape, and engages with the end of the cylindrical portion 96A of the cover member 96. In this state, the cap member 98 is screwed to the cover member 96. Thereby, the brim 92B is sandwiched and fixed between the cap member 98 and the cover member 96, and airtight sealing between the cap member 98 and the cover member 96 is kept by the brim 92B. Next, while inserting the pouched member 92 in the case main body 94, the case main body 94 and the cover member 96 are fitted to each other. Thereby, the housing case 90 formed by the case main body 94, the cover member 96, and the cap member 98 is assembled and the pouched member 92 is housed inside the housing case 90, whereby the water-feeding unit 76 is formed.

The water-feeding unit 76 is detachably attached to the coupling member 72. As shown in FIG. 7, the coupling member 72 is provided with, at the attaching position of the water-feeding unit 76, a first concave portion 72C in which the cover member 96 is fitted in and a second concave portion 72D which is formed at the center of this first concave portion 72C and the cap member 98 is fitted in are provided. The first concave portion 72C is communicated with the branched-feeding duct 78A of the air-feeding duct 78, and the second concave portion 72D is communicated with the water-feeding duct 80, and at this communicating position, the hollow pin 95 is projectedly provided. Therefore, when the water-feeding unit 76 is fitted in the coupling member 72, the pin 95 punctures the inside of the pouched member 92 via the hole 98A of the cap member 98, and the inside of the pouched member 72 is communicated with the water-feeding duct 80, and furthermore, the inside of the housing case 90 is communicated with the branched-feeding duct 78A of the air-feeding duct 78 via the air passage holes 96B of the cover member 96. When the coupling is performed as described above, a gap between the cover member 96 and the coupling member 72 and a gap between the cap member 98 and the coupling member 72 are sealed airtight by O rings 97 and 99. To secure a constant pulling-out strength between the housing case 90 and the coupling member 72, the snap fit mechanism or tube fitting mechanism can be used for coupling.

As described above, the cylinder 74 and the water-feeding unit 76 are attached to the coupling member 72. By attaching the case 70 to this coupling member 72, the air/water-feeding unit 16 is assembled. The air/water-feeding unit 16 is attached to the operation portion 14 by coupling the coupling member 72 to the air/water-feeding connector 66. After being attached, by operating the opening and closing valve 82, a gas is fed to the air-feeding duct 78 and a liquid is fed to the water-feeding duct 80.

The opening and closing valve 82 has, as schematically shown in FIG. 7, a valve 82A having grooves 82B and 82C in its outer circumferential surface, and this valve 82A is pressed to project by an elastic material 82D. When the opening and closing valve 82 is not operated, the grooves 82B and 82C of the valve 82A are positioned so as to deviate from the air-feeding duct 78 and the water-feeding duct 80, respectively. Therefore, the air-feeding duct 78 and the water-feeding duct 80 are blocked off by the valve 82A. When the opening and closing valve 82 is operated and the valve 82A is slid to position the grooves 82B and 82C at the positions of the air-feeding duct 78 and the water-feeding duct 80, the air-feeding duct 78 and the water-feeding duct 80 are communicated via the grooves 82B and 82C of the valve 82A. By using the opening and closing valve 82 thus constructed, the communication and blockage of the air-feeding duct 78 and the water-feeding duct 80 can be switched simultaneously. By providing this opening and closing valve 82, the air in the cylinder 74 and the liquid in the pouched member 92 can be prevented from wastefully flowing out when the cylinder 74 and the water-feeding unit 76 are attached. The opening and closing valve 82 can be manually operated, or can be automatically operated when the air/water-feeding unit 16 is attached to the air/water-feeding connector 66. However, when manually operating the opening and closing valve 82, it is preferable that a safety device that prohibits manual operation until the air/water-feeding unit 16 is attached to the air/water-feeding connector 66 is provided.

Figure 8C:
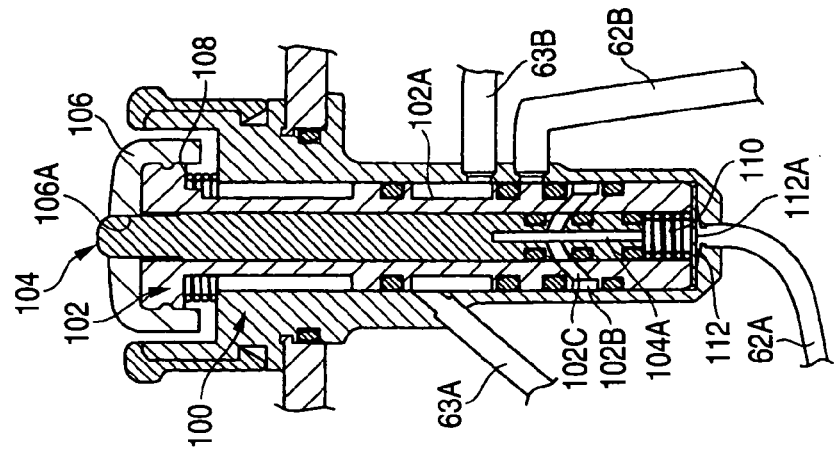
FIGS. 8A to 8C are sectional views of the construction of the air/water-feeding valve.
Figure 8B:
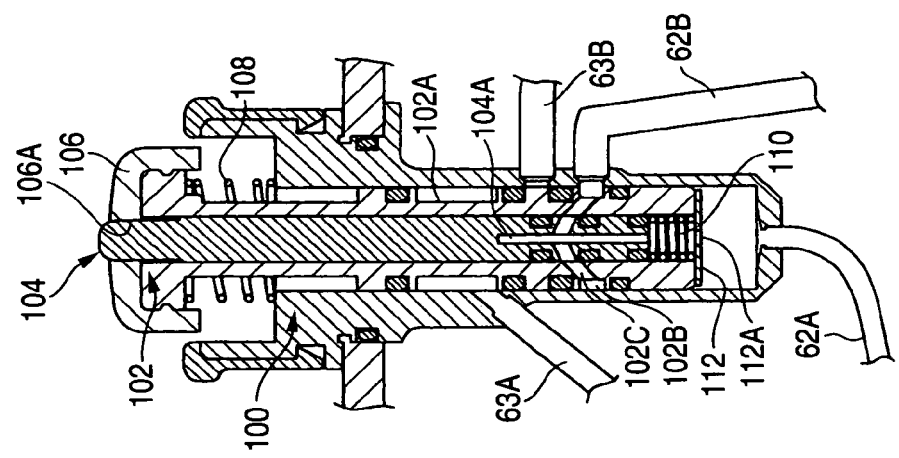
Figure 8A:
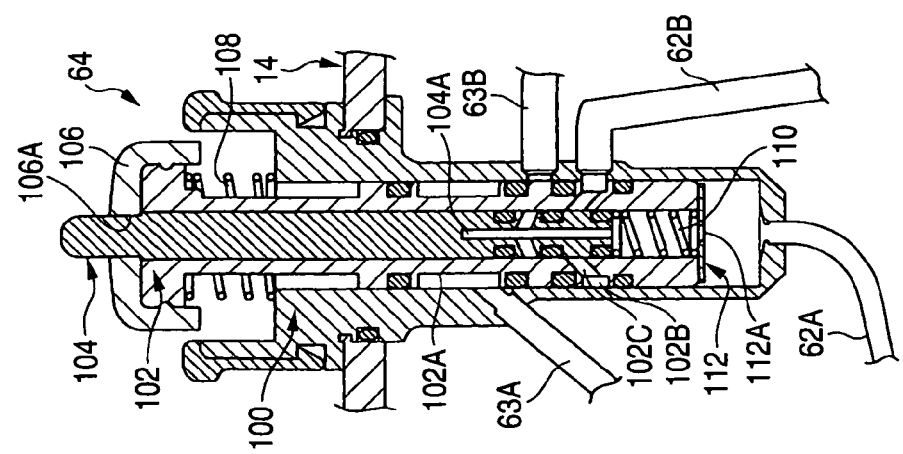

When the opening and closing valve 82 is operated after the air/water-feeding unit 16 is attached, the gas in the cylinder 74 is fed to the air-feeding tube 62B via the air-feeding duct 78, and a predetermined pressure is applied to the air-feeding tube 62B. Simultaneously, the gas in the cylinder 74 is fed to the inside of the housing case 90 (that is, between the housing case 90 and the pouched member 92) via the branched-feeding duct 78A, whereby a predetermined pressure is applied to the outside of the pouched member 92. Thereby, the liquid filled in the pouched member 92 is fed to the water-feeding tube 63B via the water-feeding duct 80, and a predetermined pressure is applied to the water-feeding tube 63B. In this state, by depressing the air/water-feeding button 20 of FIG. 3, the duct is switched by the air/water-feeding valve 64, and air/water-feeding operations are performed FIG. 8(A) through FIG. 8(C) are sectional views of the construction of the air/water-feeding valve 64. As shown in these figures, the air/water-feeding valve 64 comprises a cylinder member 100 fixed to the operation portion 14, a cylindrical outer piston member 102 slidably provided on the cylinder member 100, and an inner piston member 104 that is provided inside the outer piston member 102 and slides. A cap 106 having a hole 106A is attached to the upper end of the outer piston member 102, and the inner piston member 104 is disposed to project through the hole 106A of the cap 106. The air/water-feeding button 20 is formed by the outer piston member 102, the inner piston member 104, and the cap 106, and is detachably attached to the cylinder member 100.

The cylinder member 100 is formed into a roughly cylindrical shape, and to the bottom thereof, the air-feeding tube 62A is connected. At predetermined positions on the side surface of the cylinder member 100, the air-feeding tube 62B, the water-feeding tube 63A, and the water-feeding tube 63B are connected.

A spring 108 is provided at the upper side of the cylinder 100, and this spring 108 presses the outer piston member 102 upward. To the lower end of the outer piston member 102, a bottom plate 112 having a hole 112A is attached. On the bottom plate 112, a spring 110 is provided, and this spring 110 presses the inner piston member 104 upward. Therefore, as shown in FIG. 8(A), when the inner piston member 104 projecting from the cap 106 is depressed, the spring 110 contracts and the inner piston member 104 slides with respect to the outer piston member 106, and the inner piston member 104 is housed inside the outer piston member 102 as shown in FIG. 8(B). When the inner piston member 104 is further depressed, the spring 108 contracts and the inner piston member 104 and the outer piston member 102 simultaneously lower, and as shown in FIG. 8(C), the outer piston member 102 is housed inside the cylinder member 100. Hereinafter, the state of FIG. 8(A) is referred to as an unoperated state, the state of FIG. 8(B) is referred to as a first depressed state, and the state of FIG. 8(C) is referred to as a second depressed state.

On the outer circumferential surface of the outer piston member 102, a groove 102A is formed in one turn around the circumference. This groove 102A communicates the water-feeding tube 63A with the water-feeding tube 63B only in the second depressed state of FIG. 8(C).

In addition, on the outer circumferential surface of the outer piston member 102, a groove 102B is formed in one turn around the circumference, and furthermore, a through hole 102C pierced through the groove 102B and the inner circumferential surface of the outer piston member 102 is formed. The groove 102B is formed so as to communicate with the air-feeding tube 62B in the unoperated state of FIG. 8(A) and the first depressed state of FIG. 8(B).

On the other hand, inside the inner piston member 104, an air-feeding duct 104A that communicates the outer circumferential surface and the bottom surface of the inner piston member is formed. This air-feeding duct 104A is formed so as to communicate with the through hole 102C of the outer piston member 102 in the first depressed state of FIG. 8(B), and the through hole 102C is blocked off by the inner piston member 104 in the unoperated state of FIG. 8(A).

According to the valve structure formed as described above, in the unoperated state of FIG. 8(A), all openings of the air-feeding tubes 62A and 62B and the water-feeding tubes 63A and 63B are sealed by the outer piston member 102 or the inner piston member 104. Therefore, the gas in the air-feeding tube 62B and the liquid in the water-feeding tube 63B do not flow out, so that the gas and the liquid can be prevented from wastefully flowing out in the unoperated state.

As shown in FIG. 8(B), when the inner piston member 104 is depressed into the first depressed state, the air-feeding tube 62B is communicated with the air-feeding tube 62A via the groove 102B and the through hole 102C of the outer piston member 102, the air-feeding duct 104A of the inner piston member 104, and the hole 112A of the bottom plate 112. At this time, a gas with a predetermined pressure has been fed into the air-feeding tube 62B, so that the gas in the air-feeding tube 62B is fed into the air-feeding tube 62A. Thereby, the gas can be jetted out from the air/water-feeding nozzle 48 at the distal end of the air/water-feeding tube 60 via the air-feeding tube 62A. In the first depressed state, the water-feeding tubes 63A and 63B are blocked off by the outer piston member 102, so that the liquid is not fed.

As shown in FIG. 8(C), when the inner piston member 104 and the outer piston member 102 are depressed into the second depressed state, the position of the groove 102B of the outer piston member 102 deviates from the position of the air-feeding tube 62B and the air-feeding operation is stopped, and the water-feeding tubes 63A and 63B are communicated with each other through the groove 102A of the outer piston 102. As described above, a liquid with a predetermined pressure has been fed into the water-feeding tube 63B, so that the liquid in the water-feeding tube 63B is fed into the water-feeding tube 63A. Thereby, the liquid fed via the water-feeding tube 63A is jetted out from the air/water-feeding nozzle 48 at the distal end of the air/water-feeding tube 60.

In the water feeding operation described above, the outside of the pouched member 92 is always pressurized by a predetermined pressure by the gas from the cylinder 74, and in this state, the pressure inside the pouched member 92 is released by an operation on the air/water-feeding valve 64, whereby the pouched member 92 is pressurized by the gas outside and gradually crushed, the inner capacity thereof is gradually reduced, whereby the liquid is fed. Hereinafter, the state of the pouched member 92 in the water feeding operation is described.

FIG. 9(A) through FIG. 9(C) schematically show the internal state of the water-feeding unit 76 in the water feeding operation. As shown in FIG. 9(A), the gas fed from the cylinder 74 is fed to the inside of the housing case 90 (that is, the inside of the housing case 90 as an outside space of the pouched member 92) via the air passage holes 96B. Therefore, the outside of the pouched member 92 is pressurized by a predetermined pressure by the gas from the cylinder 74. Therefore, when the air/water-feeding valve 64 is operated into the second depressed state, the air-feeding tube 63B and the water-feeding tube 63A are communicated with each other, and the pressure inside the pouched member 92 is released, a pressure difference is generated between the inside and the outside of the pouched member 92, and the pouched member 92 is pressurized by the gas outside, gradually crushed as shown in FIG. 9(B) and FIG. 9(C), and its inner capacity is reduced. Thereby, the liquid filled inside the pouched member 92 is squeezed out and fed. At this time, the gas from the cylinder 74 is always supplied to the outside of the pouched member 92 and a predetermined pressure is always applied to the outside of the pouched member 92, so that the liquid inside the pouched member 92 is fed at a constant flow rate.

By feeding the liquid filled in the pouched member 92 by thus feeding the gas to the outside of the pouched member 92, the liquid can always be fed from the pouched member 92 regardless of the posture of the water-feeding unit 76. Therefore, the water feeding operation can be reliably performed regardless of the posture of the operation portion 14 attached with the air/water-feeding unit 16.

According to the water-feeding unit 76 described above, a liquid is filled inside the pouched member 92, and this liquid does not come into contact with the gas outside and is not contaminated. Therefore, even when a sterile water is used as the liquid in the pouched member 92, there is no possibility that the liquid is contaminated, so that a clean liquid can always be fed.

Furthermore, according to the water-feeding unit 76 described above, the inner capacity of the pouched member 92 decreases so as to squeeze out the liquid filled inside, so that the liquid in the pouched member 92 can be used to the last drop. Therefore, the amount of liquid to be housed inside the pouched member 92 can be reduced. Thereby, the water-feeding unit 76 can be reduced in size and weight, so that the operation portion 14 can be reduced in size and weight, whereby the portability is improved.

Figure 10:
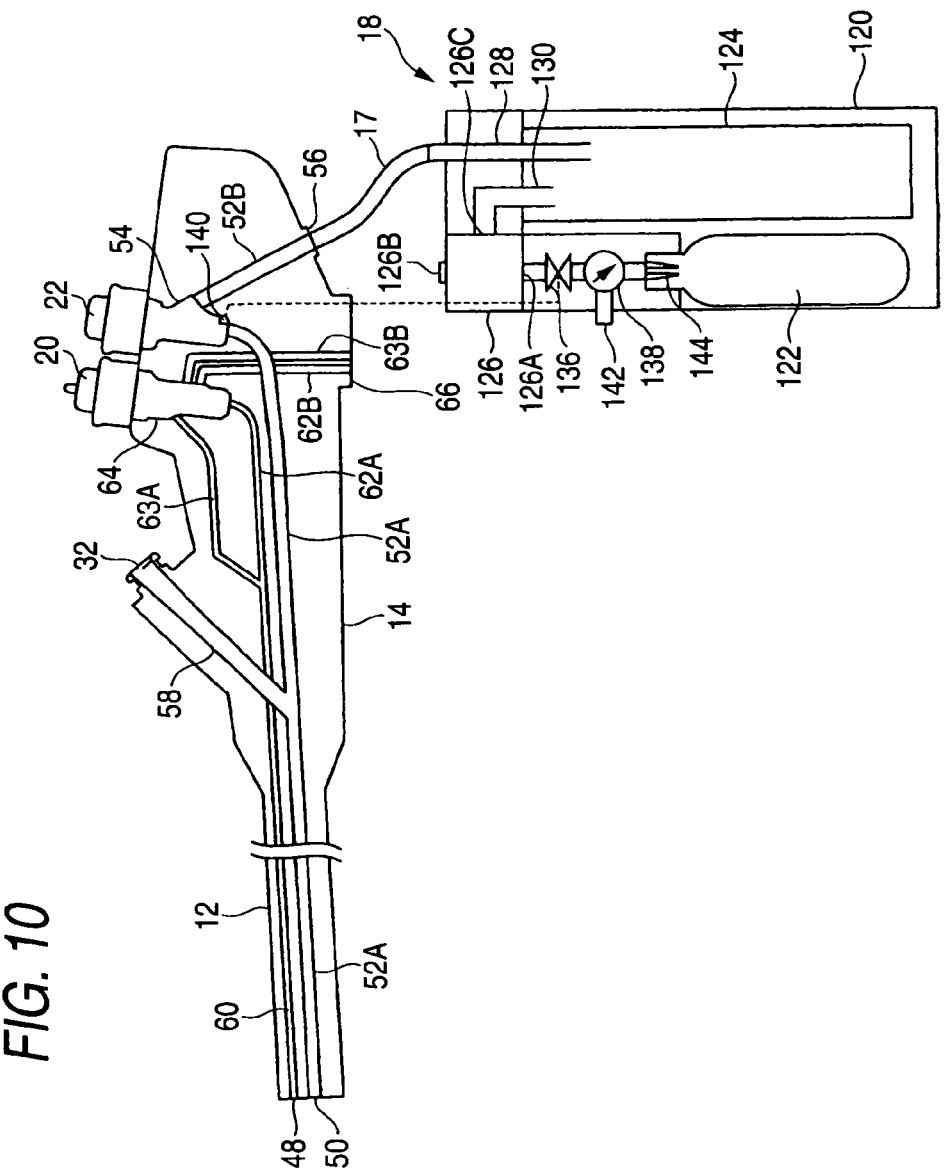
FIG. 10 is a duct construction view of a duct of a suction unit.

Next, the suction unit 18 is explained. FIG. 10 is a duct construction view schematically showing the duct of the suction unit 18. As shown in this figure, the suction unit 18 mainly comprises a cylinder 122, a liquid receiver tank 124, and a nozzle unit 126, and these are housed in a case 120 and constructed as a unit.

The case 120 of the suction unit 18 can be disposed at any location as long as it is retained without change in posture, and for example, it is attached to a belt or pocket of an operator, hung down from an engaging portion of an examination stage (bed), or hung down from a curtain rail provided above the examination stage.

To the upper side of the liquid receiver tank 124, two pipes 128 and 130 are connected. The upper end of the pipe 128 is drawn out of the case 120, and to the upper end of this pipe 128, the end of the tube 17 is detachably attached. The other end of the tube 17 is detachably connected to a suction connector 56 of the operation portion 14 of the endoscope 10. Thereby, the inside of the liquid receiver tank 124 is communicated with the suction tube 52B via the pipe 128 and the tube 17.

Figure 11:
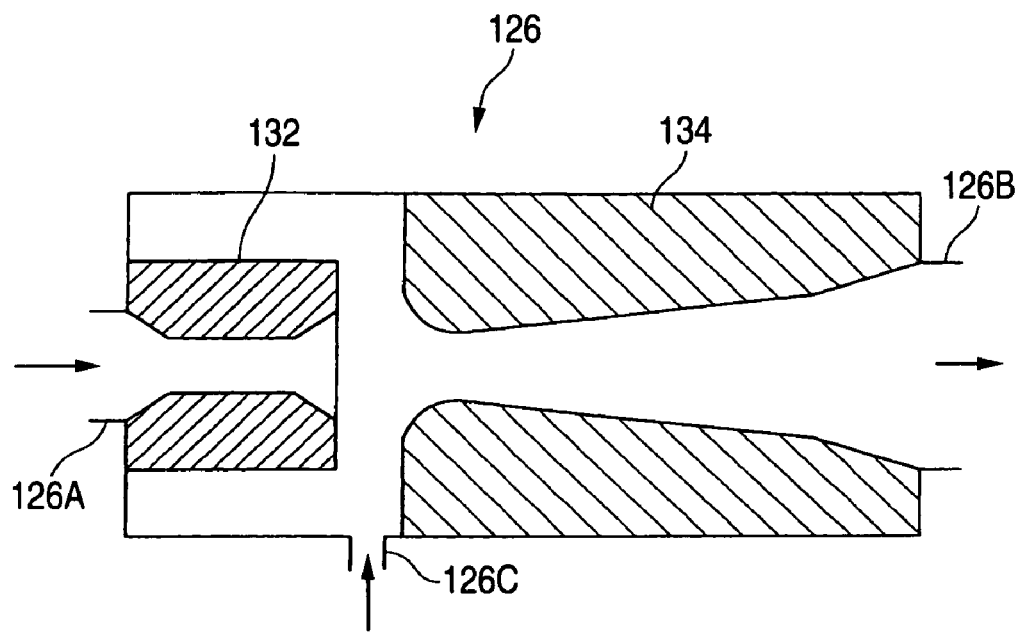
FIG. 11 is a sectional view of a construction of a nozzle unit.

On the other hand, the pipe 130 is connected to a suction port 126C of a nozzle unit 126. The nozzle unit 126 is a vacuum generator using the venturi effect, and has, as shown in FIG. 11, a nozzle 132 and a diffuser 134, and is disposed while this nozzle 132 and the diffuser 134 faces each other at a predetermined distance. At the inlet port of the nozzle 132, an air supply port 126A is provided, and at the outlet port of the diffuser 134, an exhaust port 126B is provided. In the space between the nozzle 132 and the diffuser 134, a suction port 126C is provided.

According to the nozzle unit 126 constructed as described above, when a gas is fed from the air supply port 126A, the gas is jetted from the nozzle 132 and flows into the diffuser 134, and at this time, the gas around the unit is led into the diffuser 134 and suctioned from the suction port 126C. Thereby, a suction force can be generated at the suction port 126C. The gas flown in the diffuser 134 is exhausted to the outside from the exhaust port 126B.

As shown in FIG. 10, the exhaust port 126B of the nozzle unit 126 is turned toward the outside. The suction port 126A is communicated with the cylinder 122 through a solenoid valve 136 and a regulator 138. The solenoid valve 136 is electrically connected to a sensor 140 of the suction valve 54 described later, and when the suction valve 54 is operated by the suction button 22, the sensor 140 detects this and opens the solenoid valve 136. The regulator 138 keeps the pressure of the gas flowing in the duct constant, and can adjust the pressure of the gas by using an adjust screw 142. A gas (for example, an inactive gas such as $N_2$ or $CO_2$ or air) is compressed and filled in the cylinder 122. As the cylinder 122, the same type as the cylinder 74 for air feeding can be used, or a different type can be used. The cylinder 122 is carried filled with the gas and sealed by a cover (not shown). When the cylinder 122 is screwed and attached, a hollow pin 144 is punctured through the cover of the cylinder 122 to communicate with the inside of the cylinder 122. At this time, the solenoid valve 136 is closed, so that the gas in the cylinder 122 does not wastefully leak. Then, when the solenoid valve 136 is operated, the gas in the cylinder 122 is fed to the air supply port 126A of the nozzle unit 126, and a suction force is generated at the suction port 126C of the nozzle unit 126. This suction force is transmitted to the suction tube 52B via the pipe 130, the liquid receiver tank 124, the pipe 128, and the tube 17. Then, the force is transmitted to the suction tube 52A via the suction valve 54 being operated.

FIG. 12(A) and FIG. 12(B) are sectional views showing the construction of the suction valve 54. As shown in these figures, the suction valve 54 comprises a cylinder member 150 to be fixed to the operation portion 14 and a piston member 152 slidably provided in the cylinder member 150. To the upper end of the piston member 152, a cap 154 is attached, and the suction button 22 is formed by this cap 154 and the piston member 152 and detachably attached to a cylinder member 150.

The cylinder member 150 is roughly cylindrical, and to its bottom, the suction tube 52A is connected. To a predetermined position on the side surface of the cylinder member 150, the suction tube 52B is connected. At the upper side of the cylinder member 150, a spring 156 is provided, and this spring 156 presses the piston member 152 upward. Thereby, as shown in FIG. 12(A), in the unoperated state, the piston member 152 is positioned at the upper side, and by depressing this piston member 152, as shown in FIG. 12(B), the piston member 152 is pressed into the inside of the cylinder member 150.

A flow channel 152A is formed inside the piston member 152. This flow channel 152A is formed axially from the bottom of the piston member 152, and further communicated with the side surface of the piston member 152. The flow channel 152A is formed so as to communicate with the suction tube 52B in the depressed state of FIG. 12(B), and in the unoperated state of FIG. 12(A), the suction tube 52B is blocked off by the piston member 152. The reference numeral 155 of FIG. 12(A) denotes an O ring, and this O ring 155 keeps airtightness between the inner circumferential surface of the cylinder member 150 and the outer circumferential surface of the piston member 152.

The suction valve 54 is provided with a sensor 140 that detects depression of the piston member 152. The sensor 140 comprises, for example, contact sensors 140A and 140B, and the contact sensor 140A is attached to the lower end of the piston member 152, and the contact sensor 140B is attached to the bottom of the cylinder member 150. The contact sensors 140A and 140B come into contact with each other in the depressed state of FIG. 12(B), and in response to the contact between these, the depression of the piston member 152 is detected. The construction and type of sensor 140 are not especially limited as long as it detects the depression of the piston member 152.

As described above, the sensor 140 is connected to the solenoid valve 136 of FIG. 10, and when the sensor 140 detects depression of the piston member 152, the solenoid valve 136 is operated to supply the gas to the air supply port 126A of the nozzle unit 126. Then, a suction force generated at the suction port 126C of the nozzle unit 126 is transmitted to the suction tube 52B. At this time, as shown in FIG. 12(B), the suction tube 52B is communicated with the suction tube 52A via the flow channel 152A of the piston member 152, so that the suction force inside the suction tube 52 is transmitted to the suction tube 52A. Thereby, suctioning is performed from the forceps opening 50 at the distal end of the suction tube 52A, whereby an object to be suctioned such as a body fluid or filth can be suctioned. The suctioned object is suctioned into the liquid receiver tank 124 of the suction unit 18 via the suction tubes 52A and 52B, and the tube 17. At this time, the pipe 130 is connected to the upper side of the liquid receiver tank 124, so that the suctioned object is prevented from entering the pipe 130, and the suctioned object can be prevented from entering the nozzle unit 126.

Action of the endoscope 10 constructed as described above is explained.

The endoscope 10 of this embodiment includes the suction unit 18 formed by integrating the cylinder 122, the liquid receiver tank 124, and the nozzle unit 126, and a gas in the cylinder 122 is fed to the nozzle unit 126 to generate a suction force, and by this suction force, suctioning into the inside of the liquid receiver tank 124 is performed.

Therefore, according to the embodiment, electrical power for suctioning is unnecessary, so that the power consumption of the entirety of the endoscope 10 can be reduced. Accordingly, the power consumption of the entire endoscope 10 can be reduced, and the battery to be loaded in the operation portion 14 can be made small in size and light in weight so as to have a small capacity. Thereby, according to the embodiment, the operation portion 14 can be reduced in size and weight.

In addition, according to the embodiment, the suction unit 18 is formed by integrating the cylinder 122, the liquid receiver tank 124, and the nozzle unit 126, so that the duct construction of the endoscope 10 can be simplified. Namely, the duct communicating the cylinder 122, the liquid receiver tank 124, and the nozzle unit 126 is provided inside the suction unit 18, so that the duct construction on the endoscope 10 side can be simplified. Therefore, maintenance such as cleaning and sterilization of the endoscope 10 can be performed easily.

In the embodiment described above, the air/water-feeding cylinder 74 (see FIG. 3) and the suctioning cylinder 122 (see FIG. 10) are separated from each other, however, one cylinder can be used as these. For example, in the endoscope shown in FIG. 13, the air/water-feeding cylinder 74 is commonly used as a suctioning cylinder. In the endoscope shown in this figure, the end of the suction tube 52B is disposed at the air/water-feeding connector 66. To this air/water-feeding connector 66, the air/water-feeding unit 160 including the suction section is attached.

The air/water-feeding unit 160 is mainly formed by a case 70, a coupling member 72 serving as a cover of this case 70, a cylinder 74 to be housed inside the case 70, a water-feeding unit 76, a nozzle unit 126 and a liquid receiver tank 124.

The air-feeding duct 78 inside the coupling member 72 is branched at a position closer to the cylinder 74 than the regulator 84, and in this branched-feeding duct 78B, a regulator 161 and a solenoid valve 136 are disposed. The solenoid valve 136 is electrically connected to the sensor 140 of the suction valve 54, and when the suction valve 54 is operated, the solenoid valve 136 is opened to communicate the branched-feeding duct 78B. The regulator 84 adjusts the gas flowing in the duct to a pressure suitable for an air-feeding operation, and the regulator 161 adjusts the gas flowing in the duct to a pressure suitable for a suctioning operation.

The distal end of the branched-feeding duct 78B is connected to the air supply port 126A of the nozzle unit 126. In the nozzle unit 126, an exhaust port 126B is formed outward, and a suction port 126C is connected to the liquid receiver tank 124 via the pipe 130. The liquid receiver tank 124 communicates with a pipe 128, and this pipe 128 is connected to the suction tube 52B of the operation portion 14. Therefore, when the suction force inside the suction port 126C of the nozzle unit 126 is generated, the suction force is given to the suction tube 52B via the pipe 130, the liquid receiver tank 124, and the pipe 128. Inside the liquid receiver tank 124, an air-liquid separating filter 162 is provided so as to prevent the liquid from flowing into the nozzle unit 126.

In the endoscope constructed as described above, when the suction valve 54 is operated by the suction button 22, the sensor 140 detects this and the opening and closing valve 136 is opened. Thereby, the gas in the cylinder 74 is fed into the air supply port 126A of the nozzle unit 126, and a suction force is generated at the suction port 126C. Then, this suction force is transmitted to the suction tube 52B, and further transmitted to the suction tube 52A, whereby a suctioning object such as a body fluid and filth is suctioned from the forceps opening 50 at the distal end. Thereby, the suctioning object is suctioned into the liquid receiver tank 124.

Figure 13:
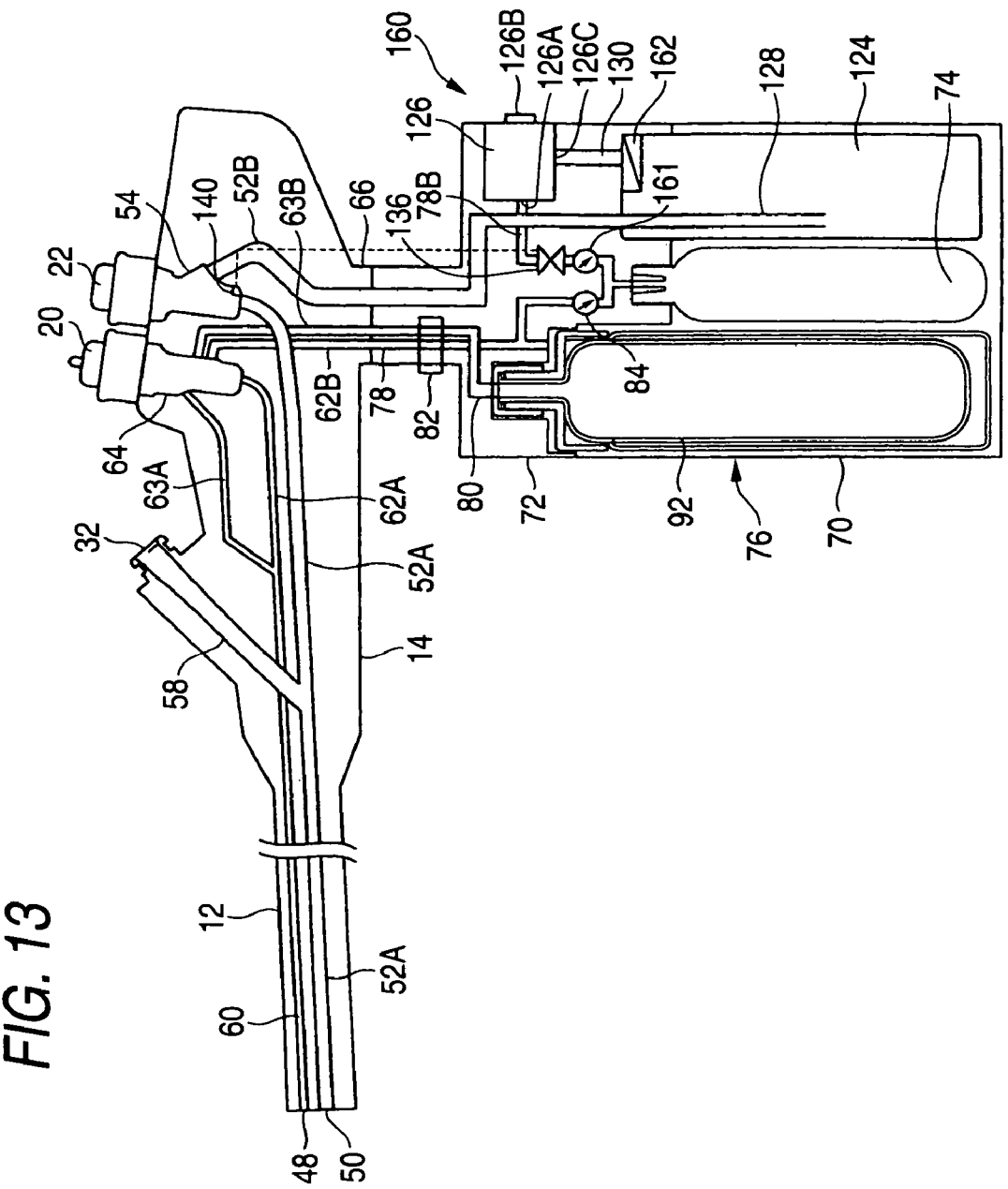
FIG. 13 is a duct construction view of an endoscope in which the air/water-feeding unit and the suction unit are formed integrally.

Thus, according to the endoscope of FIG. 13, a suctioning operation can also be performed by the cylinder 74 that performs the air and water feeding operation. According to this endoscope, the air/water-feeding unit 160 is provided with a suction section, so that by attaching the air/water-feeding unit 160 to the air/water-feeding connector 66, the air-feeding duct, the water-feeding duct, and the suction duct can be simultaneously connected. In the endoscope of FIG. 13, it is also possible that the liquid receiver tank 124 is separated from the air/water-feeding unit 160 and the liquid receiver tank 124 and the air/water-feeding unit 160 are connected to each other by using a tube or the like.

Figure 14:
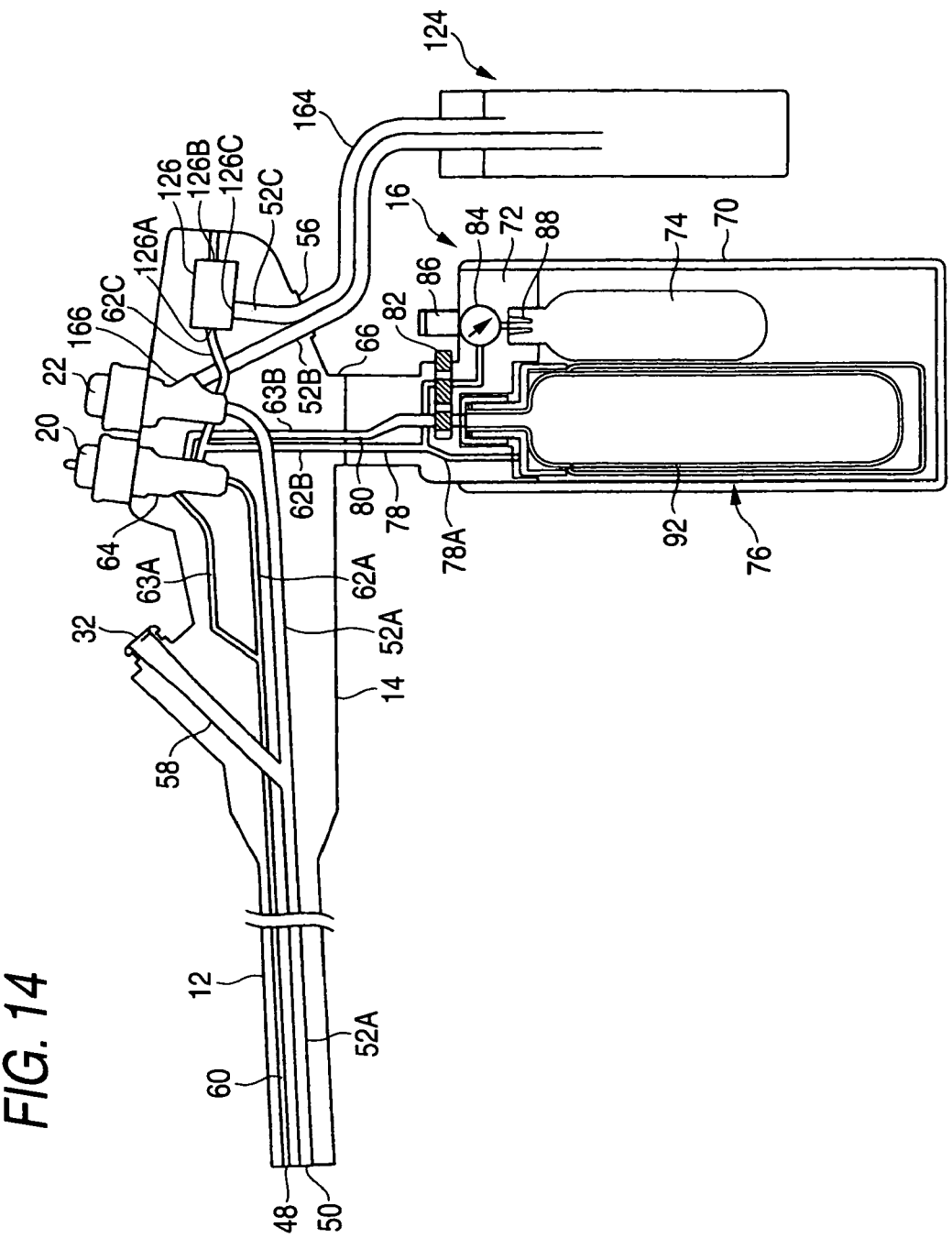
FIG. 14 is a duct construction view showing an endoscope having a construction different from FIG. 13.

FIG. 14 shows an endoscope having another construction commonly using the air/water-feeding cylinder 74 as a cylinder for suctioning. In the endoscope shown in this figure, the nozzle unit 126 is provided at the operation portion 14. The exhaust port 126B of the nozzle unit 126 is communicated with an exhaust opening formed at the proximal end of the operation portion 14. To the suction port 126C of the nozzle unit 126, the suction tube 52C is connected, and the end of this suction tube 52C is disposed at the suction connector 56. To the suction connector 56, a tube 164 having two ducts is connected, and the other end of this tube 164 is connected to the liquid receiver tank 124. A double-tube structure can be used for the tube 164.

On the other hand, to the air supply port 126A of the nozzle unit 126, the air-feeding tube 62C is connected, and this air-feeding tube 62C is connected to a suction valve 166. To the suction valve 166, the air-feeding tube 62B is branched and connected, and by operating the suction valve 166, the air-feeding tube 62B and the air-feeding tube 62C are communicated with each other.

FIG. 15(A) and FIG. 15(B) are sectional views of the construction of the suction valve 166. As shown in these figures, the suction valve 166 comprises a cylinder member 170 to be fixed to the operation portion 14, and a piston member 172 slidably provided in the cylinder member 170. A cap 174 is attached to the upper end of the piston member 172, and this cap 174 and the piston member 172 form the suction button 22.

The cylinder member 170 is roughly cylindrical, and to its bottom, the suction tube 52A is connected. To predetermined positions on the side surface of the cylinder member 170, the suction tube 52B, the air-feeding tube 62B, and the air-feeding tube 62C are connected. At the upper part of the cylinder member 170, a spring 176 is provided, and this spring 176 presses the piston member 172 upward. Therefore, as shown in FIG. 15(A), in the unoperated state, the piston member 172 is positioned at the upper side, and by depressing this piston member 172, as shown in FIG. 15(B), the piston member 172 is pressed into the cylinder member 170.

A flow channel 172A is formed inside the piston member 172. This flow channel 172A is formed axially from the bottom surface of the piston member 172, and communicated with the side surface of the piston member 172. The flow channel 172A is formed so as to communicate with the suction tube 52B in the depressed state of FIG. 15(B), and the suction tube 52B is blocked off by the piston member 172 in the unoperated state of FIG. 15(A).

On the outer circumferential surface of the piston member 172, a groove 172B is formed in one turn around the circumference. This groove 172B is formed so as to connect the air-feeding tube 62B and the air-feeding tube 62C to each other in the depressed state of FIG. 15(B). The reference numerals 177, 178, and 179 denote O rings, and keep airtightness between the inner circumferential surface of the cylinder member 170 and the outer circumferential surface of the piston member 172.

According to the suction valve 166 constructed as described above, in the unoperated state of FIG. 15(A), the openings of the air-feeding tubes 62B and 62C and the suction tubes 52A and 52B are all sealed by the piston member 172. Therefore, the high-pressure gas fed into the air-feeding tube 62 does not flow out to the outside, so that the gas in the cylinder 74 is prevented from being wastefully consumed in the unoperated state.

As shown in FIG. 15(B), when the piston member 172 is depressed, the air-feeding tube 62B and the air-feeding tube 62C are communicated with each other via the groove 172B, and the suction tube 52A and the suction tube 52B are communicated via the flow channel 172A. Due to communication between the air-feeding tube 62B and the air-feeding tube 62C, the high-pressure gas in the air-feeding tube 62B is fed into the air-feeding tube 62C. Thereby, the gas is fed to the air supply port 126A of the nozzle unit 126 of FIG. 14, so that a suction force is generated at the suction port 126C. Then, this suction force is transmitted to the suction tube 52B via the tube 52C, the tube 164, and the liquid receiver tank 124. At this time, as shown in FIG. 15(B), the suction tube 52B and the suction tube 52A are communicated with each other, so that the suction force is transmitted to the suction tube 52A, whereby suctioning object such as a body fluid and filth is suctioned from the forceps opening 50 at the distal end of the suction tube 52A. The suctioned object is fed via the suction tubes 52A and 52B and the tube 164 and stored in the liquid receiver tank 124.

According to the endoscope of FIG. 14 constructed as described above, suctioning can be performed only by switching the duct by the suction valve 166. Therefore, it is not necessary to provide a sensor on the suction valve 166.

According to the invention, a suction force is generated at the nozzle unit by using the gas in the cylinder, so that the electric power for suctioning becomes unnecessary, whereby the power consumption of the endoscope is reduced. In addition, according to the invention, a suction force is generated by the cylinder and the nozzle unit, the endoscope can be used at a site without suction equipment, whereby providing an endoscope excellent in portability.

The entire disclosure of each and every foreign patent application from which the benefit of foreign priority has been claimed in the present application is incorporated herein by reference, as if fully set forth.

What is claimed is:

1. A hand endoscope comprising:
   an insertion portion to be inserted into a body cavity;
   a hand operation portion continuously provided from a proximal end side of the insertion portion, wherein an operator holds the hand operation portion in hand; and
   a suction section that performs suction from a distal end of the insertion portion,
   wherein the suction section comprises:
   a cylinder in which a gas is compressed and filled;
   an air-feed section that feeds the gas in the cylinder to the distal end of the insertion portion:
   a nozzle unit that generates a negative pressure inside the nozzle unit by jetting out the gas in the cylinder;
   the nozzle unit including;
     a nozzle;
     a diffuser;
     an air supply port at an inlet port of the nozzle;
     an exhaust port at an outlet port of the diffuser; and
     a suction port between the nozzle and the diffuser, wherein when the gas in the cylinder is fed from the air supply port, the gas is jetted from the nozzle and flows into the diffuser with a gas around the nozzle unit being suctioned from the suction port to generate a suction force at the suction port;
   a liquid receiver tank communicated with the distal end of the insertion portion via a first pipe and tubes, and connected with the nozzle unit via a second pipe, the negative pressure inside the nozzle unit being transmitted to the liquid receiver tank, and the nozzle unit is arranged between the cylinder and the liquid receiver tank, and the exhaust port in the nozzle unit releases the gas into external air;
   an air feeding unit is entirely formed into a thin and long rectangular shape,
   the air feeding unit is disposed so that a longitudinal direction of the air feeding unit becomes orthogonal to a longitudinal direction of the hand operation portion when the air feeding unit is attached to an air feeding unit connector, and
   the air feeding unit connector is disposed on a proximal end side of the hand operation portion on a side opposite to a suction button and/or an air feeding button.

2. The hand endoscope according to claim 1,
   wherein the cylinder, the nozzle unit, and the liquid receiver tank are formed integrally as a suction unit separated from the hand operation portion.

3. The hand endoscope according to claim 1, wherein the cylinder is attached to the hand operation portion.

4. The hand endoscope according to claim 1, wherein the suction button and the air feeding button are provided adjacent each other and adjacent a function switching button of the hand operation portion.

* * * * *